United States Patent
Zhang et al.

(10) Patent No.: US 11,628,415 B2
(45) Date of Patent: Apr. 18, 2023

(54) BUILT-IN MICRO INTERFACIAL ENHANCED REACTION SYSTEM AND PROCESS FOR PTA PRODUCTION WITH PX

(71) Applicant: NANJING YANCHANG REACTION TECHNOLOGY RESEARCH INSTITUTE CO., LTD., Nanjing (CN)

(72) Inventors: Zhibing Zhang, Nanjing (CN); Zheng Zhou, Nanjing (CN); Feng Zhang, Nanjing (CN); Lei Li, Nanjing (CN); Weimin Meng, Nanjing (CN); Baorong Wang, Nanjing (CN); Gaodong Yang, Nanjing (CN); Huaxun Luo, Nanjing (CN); Guoqiang Yang, Nanjing (CN); Hongzhou Tian, Nanjing (CN); Yu Cao, Nanjing (CN)

(73) Assignee: NANJING YANCHANG REACTION TECHNOLOGY RESEARCH INSTITUTE CO., LTD., Nanjing (CN)

(*) Notice: Subject to any disclaimer, the term of this patent is extended or adjusted under 35 U.S.C. 154(b) by 413 days.

(21) Appl. No.: 16/950,914

(22) Filed: Nov. 18, 2020

(65) Prior Publication Data
US 2021/0069666 A1 Mar. 11, 2021

(30) Foreign Application Priority Data
Mar. 31, 2020 (CN) .......................... 202010243439.2

(51) Int. Cl.
*B01J 19/18* (2006.01)
*B01J 19/00* (2006.01)
(Continued)

(52) U.S. Cl.
CPC ....... *B01J 19/1806* (2013.01); *B01J 19/0013* (2013.01); *B01J 19/1862* (2013.01);
(Continued)

(58) Field of Classification Search
CPC ............... B01J 19/1806; B01J 19/0013; B01J 19/1862; B01J 2219/0004;
(Continued)

(56) References Cited

U.S. PATENT DOCUMENTS

| 5,277,878 A * | 1/1994 | Piotrowski .......... B01F 23/2368 |
| | | 261/153 |
| 2013/0036622 A1* | 2/2013 | Abraham ................. B01J 8/26 |
| | | 34/368 |

FOREIGN PATENT DOCUMENTS

CN 107346378 B * 9/2020 ............. G16C 20/10

* cited by examiner

*Primary Examiner* — Huy Tram Nguyen

(57) ABSTRACT

A built-in micro interfacial enhanced reaction system and process for PTA production with PX are provided. The system includes a reactor and a micro interfacial unit disposed inside reactor. The reactor includes a shell, an inner cylinder concentrically disposed inside shell, and a circulating heat exchange device partially disposed outside shell, inner cylinder having a bottom end connected to inner bottom surface of the shell in closed manner and an open top end, a region between shell and inner cylinder being first reaction zone, inner cylinder containing second reaction zone and third reaction zone from top to bottom, circulating heat exchange device being connected to inner cylinder and micro interfacial unit respectively. The invention can solve problems of large waste of reaction solvent acetic acid under high temperature and high pressure and being unable to take out the product TA in time during existing process of PTA production with PX.

10 Claims, 1 Drawing Sheet

(51) Int. Cl.
*C07C 45/33* (2006.01)
*C07C 51/255* (2006.01)

(52) U.S. Cl.
CPC ............ *C07C 45/33* (2013.01); *C07C 51/255* (2013.01); *B01J 2219/0004* (2013.01); *B01J 2219/00087* (2013.01)

(58) Field of Classification Search
CPC .... B01J 2219/00087; B01J 2219/00103; B01J 10/002; B01J 8/008; B01J 8/082; B01J 8/087; B01J 19/0053; B01J 19/248; B01J 2208/00176; B01J 19/0093; B01J 19/24; C07C 45/33; C07C 51/255; C07C 45/36; C07C 51/235; C07C 51/265; C07C 63/26; C07C 51/215
USPC ....................................................... 562/412
See application file for complete search history.

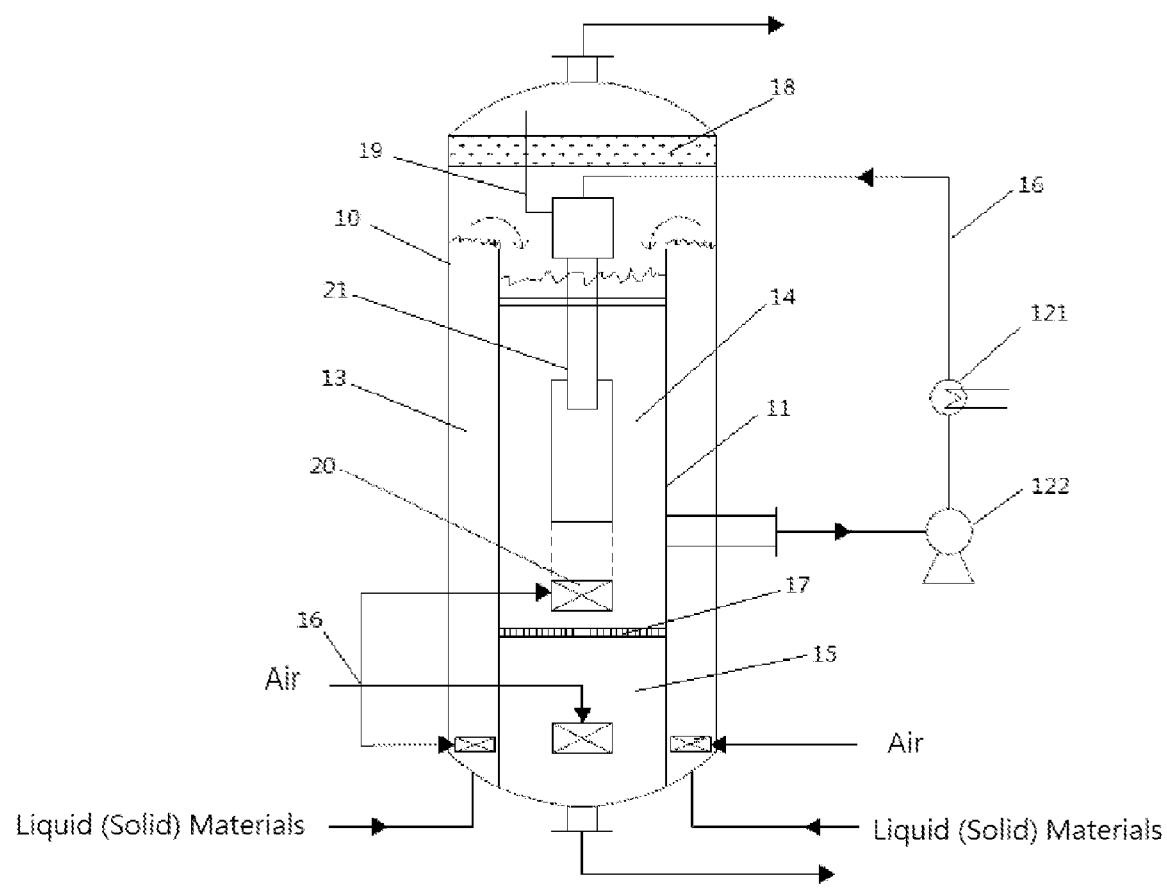

BUILT-IN MICRO INTERFACIAL ENHANCED REACTION SYSTEM AND PROCESS FOR PTA PRODUCTION WITH PX

BACKGROUND OF THE INVENTION

Field of the Invention

The present invention relates to the field of chemical technology, in particular, to a built-in micro interfacial enhanced reaction system and process for PTA production with PX.

Description of Related Art

The oxidation reaction process of using PX (para-xylene) to produce TA (terephthalic acid) is very complicated, mainly including 4 steps of Para-xylene (PX)→p-tolualdehyde (TALD)→p-toluic acid (p-TA)→p-carboxybenzaldehyde (4-CBA)→terephthalic acid (TA). The four oxidation reactions in the reaction process are series reactions, which generally use acetic acid as a solvent and cobalt acetate, manganese acetate and hydrobromic acid (or tetrabromomethane) as catalysts.

At present, in the existing PTA production technology, the 4 main steps in the oxidation reaction process are all performed in the same reactor. Although the reaction rate constants of the above 4 steps differ by more than ten times, a mixed reaction process is used without different conditions for different reactions, so that the reaction solvent acetic acid is wasted in large quantities under high temperature and high pressure, and the product TA cannot be taken out in time. Therefore, the energy consumption is high, the consumption of acetic acid is large, and the reaction efficiency is low.

SUMMARY OF THE INVENTION

It is an object of the present invention to substantially overcome or ameliorate one or more of the above disadvantages, or at least provide a useful alternative. In particular, it is an object of at least an embodiment of the present invention to provide a built-in micro interfacial enhanced reaction system for PTA production with PX that can aim at solving the problems of large waste of reaction solvent acetic acid under high temperature and high pressure and being unable to take out the product TA in time during existing process of PTA production with PX. Further it is an object of at least an embodiment of the present invention to provide a built-in micro interfacial enhanced reaction process for PTA production with PX that can aim at solving the problems of large waste of reaction solvent acetic acid under high temperature and high pressure and being unable to take out the product TA in time during existing process of PTA production with PX.

In accordance with an aspect of the present invention, there is provided a built-in micro interfacial enhanced reaction system including a reactor and a micro interfacial unit disposed inside the reactor. The reactor comprises a shell, an inner cylinder concentrically disposed inside the shell, and a circulating heat exchange device partially disposed outside the shell, the inner cylinder having a bottom end connected to an inner bottom surface of the shell in a closed manner and a top end extending toward a top end of the reactor, a region between the shell and the inner cylinder being a first reaction zone, the inner cylinder containing a second reaction zone and the third reaction zone from top to bottom, the circulating heat exchange device being connected to the inner cylinder and the micro interfacial unit respectively.

The micro interfacial unit comprises a first micro interfacial generator and a second micro interfacial generator, wherein the first micro interfacial generator is respectively disposed at bottoms of the first reaction zone, the second reaction zone and the third reaction zone for breaking an air as a reaction raw material into micro-bubbles with a diameter greater than or equal to 1 μm and less than 1 mm, and the second micro interfacial generator is disposed at an upper end of the second reaction zone and opposite to the first micro interfacial generator disposed at a bottom portion of the second reaction zone for entraining unreacted air collected at a top portion of the reactor into an interior and breaking into the micro-bubbles under the power of a reaction liquid inside the second reaction zone transported by the circulating heat exchange device.

Preferably, the first reaction zone is a reaction zone for converting p-xylene into p-tolualdehyde and for converting p-tolualdehyde into p-toluic acid, the second reaction zone is a reaction zone for converting the p-toluic acid into p-carboxybenzaldehyde, and the third reaction zone is a reaction zone for converting the p-carboxybenzaldehyde into terephthalic acid.

Preferably, a height of the inner cylinder is 4/5 of a height of the shell.

Preferably, a volume of the first reaction zone accounts for 45% of a total reaction volume in the reactor.

Preferably, a volume of the second reaction zone accounts for 53.5% of a total reaction volume in the reactor.

Preferably, a volume of the third reaction zone accounts for 1.5% of a total reaction volume in the reactor.

Preferably, the first micro interfacial generator is pneumatically-actuated, and the second micro interfacial generator is hydraulically-actuated.

In accordance with another aspect of the present invention, there is provided a built-in micro interfacial enhanced reaction process for PTA production with PX. The process includes steps of:

passing a mixture of p-xylene, acetic acid and a catalyst through a bottom end of a reactor into a first reaction zone between a shell and an inner cylinder of the reactor while passing air into a micro interfacial generator at a bottom portion of the first reaction zone to break the air into the micro-bubbles with a diameter greater than or equal to 1 μm and less than 1 mm for forming an emulsion with a liquid material, and simultaneously converting p-xylene into p-tolualdehyde and p-tolualdehyde into p-toluic acid, wherein the unreacted air leaves the liquid level and rises above the reactor;

overflowing a reaction mixed solution from the first reaction zone into the inner cylinder with the continuous progress of the above reaction in the first reaction zone while introducing the air broken into the micro-bubbles into the zone through the first micro interfacial generator disposed at the bottom portion of a second reaction zone on the top portion of the inner cylinder and reacting with the p-toluic acid in the mixed solution to form p-carboxybenzaldehyde under action of the catalyst, wherein the unreacted air leaves the liquid level and rises above the reactor, and is fed into the bottom portion of the zone for continuous participation in the formation of the p-carboxybenzaldehyde by an airway through entrainment of the second micro interfacial generator disposed in the top portion of the second reaction zone under power of the circulating heat exchange device; and passing the p-carboxybenzaldehyde generated by the reaction in the second reaction zone through a wave protection grid to enter a third reaction zone below the zone to react with the micro-bubbles passed through the first micro interfacial generator disposed at the bottom portion of the zone under the action of the catalyst to generate terephthalic acid and to be discharged through an outlet below the reactor together with the unreacted reaction mixture for entering the subsequent separation and refining section.

Preferably, a volume of the first reaction zone accounts for 45% of a total reaction volume in the reactor, a volume of the second reaction zone accounts for 53.5% of a total reaction volume in the reactor, and a volume of the third reaction zone accounts for 1.5% of a total reaction volume in the reactor.

Preferably, the first micro interfacial generator is pneumatically-actuated, and the second micro interfacial generator is hydraulically-actuated.

Compared to the prior art, the built-in micro interfacial enhanced reaction system and process for PTA production with PX of at least an embodiment of the present invention have the following advantages: the a built-in micro interfacial enhanced reaction system and process for PTA production with PX of the present invention adopts a segmented reaction concept with the consideration of the difference in the four-step reaction rate of PTA production with PX, wherein the inside of the reactor is arranged into three different reaction zones having different reaction steps for each so that different conditions are given for different reaction stages in the same reactor and particularly the contradiction that acetic acid solvent cannot withstand high temperature oxidation conditions is solved, and with water as the solvent for p-TA oxidation reaction, the problems of large waste of reaction solvent acetic acid under high temperature and high pressure and being unable to take out the product TA in time during the existing process of PTA production with PX are solved, thereby greatly reducing energy consumption, saving acetic acid solvent, and improving reaction efficiency.

In particular, for the built-in micro interfacial enhanced reaction system and process for PTA production with PX of the present invention, by arranging micro-interface generators in each reaction zone inside the reactor and crushing the air inside each reactor to make it break into micro-bubbles with a diameter greater than or equal to 1 μm and less than 1 mm for forming an emulsion with liquid materials, the mass transfer area between air and liquid materials is effectively increased, the thickness of the liquid film is reduced, and the mass transfer resistance is decreased, so as to further effectively reduce energy consumption and improve reaction efficiency.

Further, for the built-in micro interfacial enhanced reaction system and process for PTA production with PX of the present invention, by arranging the circulating heat exchange device to effectively control the temperature of the reaction process during the reaction process while ensuring the uniformity of mixing between the reaction materials inside the reactor, the reactants may be ensured to fully participate in the reaction, thereby greatly improving the utilization of the reactants while preventing side reactions caused by uneven local temperature as well as improving the quality of the product to a certain extent.

BRIEF DESCRIPTION OF THE DRAWINGS

Aspects of the present invention are best understood from the following detailed description when read with the accompanying FIGURES. The exemplary embodiments of the present invention and the description thereof are used to explain the present invention, and do not constitute improper limitations on the preset invention. In the drawings:

FIG. 1 is a structural diagram of a built-in micro interfacial enhanced reaction system for PTA production with PX according to an embodiment of the present invention.

DESCRIPTION OF THE PREFERRED EMBODIMENTS

It should be noted that, in the case of no conflicts, the embodiments and features in the embodiments of the preset invention can be combined mutually.

The present invention is described in detail with reference to drawings and with combination of embodiments.

EMBODIMENTS

With reference to FIG. 1, a built-in micro interfacial enhanced reaction system for PTA production with PX according to an embodiment of the invention is shown, including: a reactor and a micro interfacial unit disposed inside the reactor.

The reactor includes a shell 10, an inner cylinder 11 disposed inside the shell 10, and a circulating heat exchange device. A bottom end of the inner cylinder 11 is connected on an inner bottom surface of the shell 10 and has a top end opened. A region between the sell 10 and the inner cylinder 11 is a first reaction zone 13, wherein the first reaction zone 13 is a reaction zone for converting p-xylene into p-tolualdehyde and for converting p-tolualdehyde into p-toluic acid (i.e., the first two steps of oxidation reaction of PTA production with PX). The inner cylinder 11 contains a second reaction zone 14 and a third reaction zone 15 from top to bottom, wherein the second reaction zone 14 is a reaction zone for converting the p-toluic acid into p-carboxybenzaldehyde (i.e., the third step of oxidation reaction of PTA production with PX), and the third reaction zone 15 is a reaction zone for converting p-carboxybenzaldehyde into terephthalic acid (i.e., the fourth step of oxidation reaction of PTA production with PX). The circulating heat exchange device is connected to the inner cylinder 11 and the micro interfacial unit respectively, and is formed by connecting a heat exchanger 121 and a pressure pump 122 through a pipe 16 to effectively control the temperature during the reaction process while ensuring the uniformity of mixing between the reaction materials inside the reactor and full participation of the reactants in the reaction, so as to further greatly improve the utilization rate of the reactants while preventing the occurrence of side reactions caused by uneven local temperature as well as improving the quality of the product to a certain extent. In addition, the top portion of the shell 10 is further provided with an exhaust channel, with the bottom portion provided for taking out a mixture material containing the terephthalic acid reaction product from the third reaction zone 15. It is to be understood that the present invention adopts a segmented reaction concept with the consideration of the difference in the four-step reaction rate of PTA production with PX, wherein the inside of the reactor is disposed into three different reaction zones (first reaction zone, second reaction zone and third reaction zone) having different reaction steps for each so that different conditions are given for different reaction stages in the same reactor and particularly the contradiction that acetic acid solvent cannot withstand high temperature oxidation conditions is solved, and with water as the solvent for p-TA oxidation reaction, the problems of large waste of reaction solvent acetic acid under high temperature and high pressure and being unable to take out the product TA in time during the existing process of PTA production with PX are solved, thereby greatly reducing energy consumption, saving acetic acid solvent, and improving reaction efficiency.

In this embodiment, the invention includes the shell 10, the inner cylinder 11 concentrically disposed inside the shell 10, and the circulating heat exchange device partially disposed outside the shell 10. The inner cylinder 11 has a bottom end connected to an inner bottom surface of the shell 10 in a closed manner, and a top end that is opened and extends upwards in an axial direction of the reactor to 4/5 of a height of the shell 10. A circular region between the shell 10 and the inner cylinder 11 is a first reaction zone 13 for the first two steps of oxidation reaction of PTA production with PX, and a volume of the first reaction zone accounts for 45% of a total reaction volume in the reactor. The inner cylinder 11 contains a second reaction zone 14 for the third step of oxidation reaction of PTA production with PX and the third reaction zone 15 for the fourth step of oxidation reaction of PTA production with PX from top to bottom in turn, wherein a volume of the second reaction zone accounts for 53.5% of a total reaction volume in the reactor, and a volume of the third reaction zone accounts for 1.5% of a total reaction volume in the reactor. A wave protection grid 17 is provided between two zones. The circulating heat exchange device is connected to the inner cylinder 11 and the micro interfacial unit respectively, and is formed by connecting a heat exchanger 121 and a pressure pump 122 through a pipe 16 to effectively control the temperature during the reaction process and to offer power for the second micro interfacial generator connected therewith while ensuring the uniformity of mixing between the reaction materials inside the reactor, the reactants may be ensured to fully participate in the reaction, thereby greatly improving the utilization of the reactants while preventing side reactions caused by uneven local temperature as well as improving the quality of the product to a certain extent. In addition, an top portion of the shell 10 is further provided with a defoaming net 16, with the top end further provided with an exhaust channel, with the bottom portion provided for taking out a mixture material containing the terephthalic acid reaction product from the third reaction zone 15. It should be understood that the present embodiment adopts a segmented reaction concept with the consideration of the difference in the four-step reaction rate of PTA production with PX, wherein the inside of the reactor is disposed into three different reaction zones (first reaction zone, second reaction zone and third reaction zone) having different reaction steps for each so that different conditions are given for different reaction stages in the same reactor and particularly the reaction volume of each reaction zone is determined according to the reaction difficulty or reaction time of different reaction stages, so as to effectively ensure that all reactions in the process of PTA production with PX may be fully performed, thereby further solving the contradiction that acetic acid solvent may not withstand high temperature oxidation conditions while greatly improving the reaction efficiency of each reaction zone and finally effectively increasing the output rate of the product.

The micro interfacial unit includes a first micro interfacial generator 20 and a second micro interfacial generator 21, wherein the first micro interfacial generator 20 is respectively disposed at bottoms of the first reaction zone 13, the second reaction zone 14 and the third reaction zone 15 for breaking an air as a reaction raw material into micro-bubbles with a diameter greater than or equal to 1 μm and less than 1 mm in each reactor zone inside the reactor so as to provide the reactions of different stages with the reaction raw materials. The second micro interfacial generator 21 is disposed at an upper end of the second reaction zone 14 and opposite to the first micro interfacial generator 20 disposed at a bottom portion of the second reaction zone 14 for entraining unreacted air collected at a top portion of the reactor into an interior and breaking into the micro-bubbles under the power of a reaction liquid inside the second reaction zone 14 transported by the circulating heat exchange device. The specific structure of the micro interfacial generator is embodied in the prior patents of the inventor, such as the patent of publication No. 106215730A. The core of the micro interfacial generator is bubble breakage, which will not be repeated here. Regarding the reaction mechanism and control method of the micro interfacial generator 4, it has been disclosed in the prior patent CN107563051B of the inventor of the present invention, which will not be repeated here. It is to be understood that in the present invention, by arranging micro-interface generators in each reaction zone inside the reactor and crushing the air inside each reaction zone to make it break into micro-bubbles with a diameter greater than or equal to 1 μm and less than 1 mm for forming an emulsion with liquid materials, the mass transfer area between air and liquid materials is effectively increased, the thickness of the liquid film is reduced, and the mass transfer resistance is decreased, so as to further effectively reduce energy consumption and improve reaction efficiency.

This embodiment includes the first micro interfacial generator 20 and the second micro interfacial generator 21, wherein the first micro interfacial generator 20 is a pneumatically-actuated micro interfacial generator and respectively disposed at bottoms of the first reaction zone 13, the second reaction zone 14 and the third reaction zone 15 for breaking an air as a reaction raw material into micro-bubbles with a diameter greater than or equal to 1 μm and less than 1 mm in each reactor zone inside the reactor so as to provide the reactions of different stages with the reaction raw materials. The second micro interfacial generator 21 is an hydraulically-actuated micro interfacial generator and disposed at an upper end of the second reaction zone 14 and opposite to the first micro interfacial generator 20 disposed at a bottom portion of the second reaction zone 14 for entraining unreacted air collected at a top portion of the reactor into an interior and breaking into the micro-bubbles under the power of a reaction liquid inside the second reaction zone 14 transported by the circulating heat exchange device. It is to be understood that in the present embodiment, by arranging micro-interface generators in each reaction zone inside the reactor and crushing the air inside each reaction zone to make it break into micro-bubbles with a diameter greater than or equal to 1 μm and less than 1 mm for forming an emulsion with liquid materials, the mass transfer area between air and liquid materials is effectively increased, the thickness of the liquid film is reduced, and the mass transfer resistance is decreased, so as to further effectively reduce energy consumption and improve reaction efficiency.

With combination of FIG. 1, a working flow of the built-in micro interfacial enhanced reaction system for PTA production with PX of this embodiment is:

First, a mixture of the raw materials of P-xylene, acetic acid and catalysts (cobalt acetate, manganese acetate, hydrobromic acid) enters into the first reaction zone 13 between the shell 10 and the inner cylinder 11 of the reactor through the bottom end of the reactor (the volume of the zone accounts for 45% of the total reaction volume in the reactor as the time required for the first two steps of PTA production with PX is about 45% of the total time of all four steps)

while the air entering into the first micro interfacial generator 20 at the bottom portion of the first reaction zone 13 in the reactor to be broken into micro-bubbles with a diameter greater than or equal to 1 μm and less than 1 mm and mixed with the liquid materials in the zone to form an emulsion, so as to effectively increase the contact area between the air and the liquid reaction materials and further promote the reaction in the zone. The first two steps of the reaction of PTA production with PX are performed in the zone, i.e., the p-xylene is converted to p-tolualdehyde and p-tolualdehyde is converted to p-toluic acid, and overflows into the inner cylinder, and the unreacted gas leaves the liquid surface (wave line) and passes through the defoaming net 18 to rise above the reactor. In the zone, the fluid is in a stable flat push flow, which mainly completes the first step of PX→TALD and the second step of TALD→p-TA.

Then, the air broken into the micro-bubbles is introduced into the zone through the first micro interfacial generator disposed at the bottom portion of the second reaction zone on the top portion of the inner cylinder to be mixed with the liquid materials in the zone to form an emulsion and reacted with the p-toluic acid in the mixed liquid under the action of the catalyst to form p-carboxybenzaldehyde, wherein the unreacted gas leaves the liquid surface (wave line) and passes through the defoaming net 18 to rise above the reactor. The unreacted air leaves the liquid level and rises above the reactor, is fed into the bottom portion of the second reaction zone 14 of the top portion inside the inner cylinder 11 for continuous reaction by an airway 19 through the entrainment of the second micro interfacial generator 21 disposed in the top portion of the second reaction zone 14 under the power of the circulating heat exchange device, and then enters the exhaust processing unit from the outlet at the top portion of the reactor as the exhaust under the pressure after many cycles, thereby improving the utilization of oxygen in the air. In the zone, with severe fully-mixed flow generated by two micro interfacial generators that are opposed from the top and bottom (first micro interfacial generator 20 and second micro interfacial generator 21), the third step of p-TA→4-CBA is performed (this step has the slowest reaction speed, so it is necessary to create a fully-mixed flow effect to enhance mass transfer and accelerate the reaction. And the volume of the zone accounts for 53.5% of the total reaction volume in the reactor, for the same reason as above). At the same time, the materials in the zone are controlled in terms of temperature by the circulating heat exchange device outside the reactor, the bubbles generated by the second micro interfacial generator 21 in the second reaction zone 14 move downward, and the bubbles generated by the first micro interfacial generator 20 move upward. The two bubbles collide violently, which intensifies the turbulence of the fluid, produces smaller bubbles, further increases the contact area of the gas-liquid, and accelerates the mass transfer and reaction.

Finally, the product in the second reaction zone 14 enters the third reaction zone 15 through the wave protection grid 17 (the volume of the zone accounts for 1.5% of the total reaction volume in the reactor, for the same reason as above). Due to the action of the wave protection grid 17, the region is turned into flat push flow again, and the fourth step of 4-CBA→TA is performed, i.e., p-carboxybenzaldehyde is converted into terephthalic acid. The air enters the reaction zone through the first micro interfacial generator 20 at the bottom of the reaction zone to perform oxidation reaction. The reaction product (terephthalic acid TA) together with unreacted p-xylene PX, solvent, catalyst and by-products are discharged through the outlet pipe below the reactor for the subsequent separation and refining section.

Obviously, it can be seen that the built-in micro interfacial enhanced reaction system and process for PTA production with PX provided by the present invention adopt a segmented reaction concept with the consideration of the difference in the four-step reaction rate of PTA production with PX, wherein the inside of the reactor is disposed into three different reaction zones having different reaction steps for each so that different conditions are given for different reaction stages in the same reactor and particularly the contradiction that acetic acid solvent cannot withstand high temperature oxidation conditions is solved, and with water as the solvent for p-TA oxidation reaction, the problems of large waste of reaction solvent acetic acid under high temperature and high pressure and being unable to take out the product TA in time during the existing process of PTA production with PX are solved, thereby greatly reducing energy consumption, saving acetic acid solvent, and improving reaction efficiency.

In particular, for the built-in micro interfacial enhanced system and process for PTA production with PX in the present invention, by arranging micro-interface generators in each reaction zone inside the reactor and crushing the air inside each reactor to make it break into micro-bubbles with a diameter greater than or equal to 1 μm and less than 1 mm for forming an emulsion with liquid materials, the mass transfer area between air and liquid materials is effectively increased, the thickness of the liquid film is reduced, and the mass transfer resistance is decreased, so as to further effectively reduce energy consumption and improve reaction efficiency.

Further, for the built-in micro interfacial enhanced system and process for PTA production with PX in the present invention, by arranging the circulating heat exchange device to effectively control the temperature of the reaction process during the reaction process while ensuring the uniformity of mixing between the reaction materials inside the reactor, the reactants may be ensured to fully participate in the reaction, thereby greatly improving the utilization of the reactants while preventing side reactions caused by uneven local temperature as well as improving the quality of the product to a certain extent.

Obviously, those skilled in the art can make various changes and modifications to the present invention without departing from the spirit and scope of the present invention. In this way, if these changes and modifications of the present invention fall within the scope of the present invention and their equivalent technologies, the present invention is also intended to include these changes and modifications.

The invention claimed is:

1. A built-in micro interfacial enhanced reaction system for PTA production with PX, comprising: a reactor and a micro interfacial unit disposed inside the reactor; wherein
   the reactor comprises a shell, an inner cylinder concentrically disposed inside the shell, and a circulating heat exchange device partially disposed outside the shell, the inner cylinder having a bottom end connected to an inner bottom surface of the shell in a closed manner and a top end extending toward a top end of the reactor, a region between the shell and the inner cylinder being a first reaction zone, the inner cylinder containing a second reaction zone and a third reaction zone from top to bottom, the circulating heat exchange device being connected to the inner cylinder and the micro interfacial unit respectively;

the micro interfacial unit comprises a first micro interfacial generator and a second micro interfacial generator, wherein the first micro interfacial generator is respectively disposed at bottom portions of the first reaction zone, the second reaction zone and the third reaction zone for breaking air as a reaction raw material into micro-bubbles with a diameter greater than or equal to 1 μm and less than 1 mm, and the second micro interfacial generator is disposed at an upper end of the second reaction zone and opposite to the first micro interfacial generator disposed at the bottom portion of the second reaction zone for entraining unreacted air collected at a top portion of the reactor into an interior and breaking into the micro-bubbles under power of a reaction liquid inside the second reaction zone transported by the circulating heat exchange device.

2. The built-in micro interfacial enhanced reaction system for PTA production with PX according to claim 1, wherein the first reaction zone is a reaction zone for converting p-xylene into p-tolualdehyde and for converting p-tolualdehyde into p-toluic acid, the second reaction zone is a reaction zone for converting the p-toluic acid into p-carboxybenzaldehyde, and the third reaction zone is a reaction zone for converting the p-carboxybenzaldehyde into terephthalic acid.

3. The built-in micro interfacial enhanced reaction system for PTA production with PX according to claim 2, wherein a height of the inner cylinder is 4/5 of a height of the shell.

4. The built-in micro interfacial enhanced reaction system for PTA production with PX according to claim 3, wherein a volume of the first reaction zone accounts for 45% of a total reaction volume in the reactor.

5. The built-in micro interfacial enhanced reaction system for PTA production with PX according to claim 3, wherein a volume of the second reaction zone accounts for 53.5% of a total reaction volume in the reactor.

6. The built-in micro interfacial enhanced reaction system for PTA production with PX according to claim 3, wherein a volume of the third reaction zone accounts for 1.5% of a total reaction volume in the reactor.

7. The built-in micro interfacial enhanced reaction system for PTA production with PX according to claim 1, wherein the first micro interfacial generator is pneumatically-actuated, and the second micro interfacial generator is hydraulically-actuated.

8. A built-in micro interfacial enhanced reaction process for PTA production with PX, comprising steps of:
passing a mixture of p-xylene, acetic acid and a catalyst through a bottom end of a reactor into a first reaction zone between a shell and an inner cylinder of the reactor while passing air into a micro interfacial generator at a bottom portion of the first reaction zone to break the air into the micro-bubbles with a diameter greater than or equal to 1 μm and less than 1 mm for forming an emulsion with a liquid material, and simultaneously converting p-xylene into p-tolualdehyde and p-tolualdehyde into p-toluic acid, wherein the unreacted air leaves the liquid level and rises above the reactor;

overflowing a reaction mixed solution from the first reaction zone into the inner cylinder with the continuous progress of the above reaction in the first reaction zone while introducing the air broken into the micro-bubbles into the zone through the first micro interfacial generator disposed at the bottom portion of a second reaction zone on the top portion of the inner cylinder and reacting with the p-toluic acid in the mixed solution to form p-carboxybenzaldehyde under action of the catalyst, wherein the unreacted air leaves the liquid level and rises above the reactor, and is fed into the bottom portion of the zone for continuous participation in the formation of the p-carboxybenzaldehyde by an airway through entrainment of the second micro interfacial generator disposed in the top portion of the second reaction zone under power of the circulating heat exchange device; and passing the p-carboxybenzaldehyde generated by the reaction in the second reaction zone through a wave protection grid to enter a third reaction zone below the zone to react with the micro-bubbles passed through the first micro interfacial generator disposed at the bottom portion of the zone under the action of the catalyst to generate terephthalic acid and to be discharged through an outlet below the reactor together with the unreacted reaction mixture for entering the subsequent separation and refining section.

9. The built-in micro interfacial enhanced reaction process for PTA production with PX according to claim 8, wherein a volume of the first reaction zone accounts for 45% of a total reaction volume in the reactor, a volume of the second reaction zone accounts for 53.5% of a total reaction volume in the reactor, and a volume of the third reaction zone accounts for 1.5% of a total reaction volume in the reactor.

10. The built-in micro interfacial enhanced reaction process for PTA production with PX according to claim 8, wherein the first micro interfacial generator is pneumatically-actuated, and the second micro interfacial generator is hydraulically-actuated.

* * * * *